United States Patent
Singh

(10) Patent No.: US 10,213,391 B2
(45) Date of Patent: Feb. 26, 2019

(54) PHARMACEUTICAL COMPOSITIONS COMPRISING HEMP AND TURMERIC TO TREAT PAIN AND INFLAMMATION

(71) Applicant: Mewa Singh, Zachary, LA (US)

(72) Inventor: Mewa Singh, Zachary, LA (US)

(*) Notice: Subject to any disclaimer, the term of this patent is extended or adjusted under 35 U.S.C. 154(b) by 313 days.

(21) Appl. No.: 15/307,124

(22) PCT Filed: May 1, 2015

(86) PCT No.: PCT/US2015/028718
§ 371 (c)(1),
(2) Date: Oct. 27, 2016

(87) PCT Pub. No.: WO2015/171445
PCT Pub. Date: Nov. 12, 2015

(65) Prior Publication Data
US 2017/0042835 A1   Feb. 16, 2017

Related U.S. Application Data

(60) Provisional application No. 61/989,158, filed on May 6, 2014.

(51) Int. Cl.
| | | |
|---|---|---|
| A61K 36/00 | (2006.01) | |
| A61K 31/12 | (2006.01) | |
| A61K 36/9066 | (2006.01) | |
| A61K 31/352 | (2006.01) | |
| A61K 9/00 | (2006.01) | |
| A61K 9/28 | (2006.01) | |
| A61K 9/48 | (2006.01) | |
| A61K 36/9068 | (2006.01) | |
| A61K 31/121 | (2006.01) | |
| A61K 9/20 | (2006.01) | |
| A61K 31/047 | (2006.01) | |
| A61K 33/06 | (2006.01) | |
| A61K 36/185 | (2006.01) | |

(52) U.S. Cl.
CPC .......... *A61K 31/12* (2013.01); *A61K 9/0095* (2013.01); *A61K 9/2009* (2013.01); *A61K 9/2013* (2013.01); *A61K 9/2027* (2013.01); *A61K 9/2036* (2013.01); *A61K 9/2054* (2013.01); *A61K 9/2059* (2013.01); *A61K 9/2846* (2013.01); *A61K 9/485* (2013.01); *A61K 9/4866* (2013.01); *A61K 31/047* (2013.01); *A61K 31/121* (2013.01); *A61K 31/352* (2013.01); *A61K 33/06* (2013.01); *A61K 36/185* (2013.01); *A61K 36/9066* (2013.01); *A61K 36/9068* (2013.01)

(58) Field of Classification Search
CPC .................................................... A61K 36/00

USPC ......................................................... 424/725
See application file for complete search history.

(56) References Cited

U.S. PATENT DOCUMENTS

| 2011/0028431 A1 | 2/2011 | Zerbe et al. |
| 2012/0270845 A1 | 10/2012 | Bannister et al. |

FOREIGN PATENT DOCUMENTS

| IE | 84610 B | * 6/2007 |
| WO | 2012175518 A1 | 12/2012 |
| WO | 2013006729 A2 | 1/2013 |
| WO | 2013108254 A1 | 7/2013 |
| WO | 2013172999 A1 | 11/2013 |

OTHER PUBLICATIONS

International Search Report re PCT/US2015/028718,K dated Jul. 24, 2015.
Julie S. Jurenka, MT(ASCP), "Anti-inflammatory Properties of Curcumin, a Major Constituent of Curcuma longa: A Review of Predinical and Clinical Research", Alternative Medicine Review vol. 14, No. 2 2009, 141-153.
George W. Booz, "Cannabidiol as an Emergent Therapeutic Strategy for Lessening the Impact of Inflammation on Oxidative Stress", Free Radic Biol Med. Sep. 1, 2011; 51(5): 1054-1061. doi:10.1016/j.freeradbiomed.2011.01.007.
Wei Xiong, et al., "Cannabinoids suppress inflammatory and neuropathic pain by targeting α3 glycine receptors", The Journal of Experimental Science, The Rockefeller University Press, vol. 209 No. 6, 1121-1134, Sep. 2012, 10.1084/jem.20120242.
Zili Zhang, et al, "Curcumin modulates cannabinoid receptors in liver fibrosis in vivo and inhibits extracellular matrix expression in hepatic stellate cells by suppressing cannabinoid receptor type-1 in vitro", European Journal of Pharmacology, 721 (2013) 133-140.
Bharat B. Aggarwal, et al, "Potential Therapeutic Effects of Curcumin, the Anti-inflammatory Agent, Against Neurodegenerative, Cardiovascular, Pulmonary, Metabolic, Autoimmune and Neoplastic Diseases", Int J Biochem Cell Biol. 2009 ; 41(1): 40-59. doi:10.1016/j.biocel.2008.06.010.
Zahao, X., et al., "Curcumin exerts antinociceptive effects in a mouse model of neuropathic pain: descending monoamine system and opioid receptors are differentially involved", Neuropharmacology, Feb. 2012 62(2): 843-54.

* cited by examiner

Primary Examiner — Michael V Meller
(74) Attorney, Agent, or Firm — Caesar Rivise, PC

(57) ABSTRACT

The present invention comprises compositions comprising therapeutically effective amounts of CBD and curcumin in various combinations to treat pain. CBD and curcumin are preferably from natural sources. A method of using the combination of CBD and curcumin compositions to treat pain is also described.

18 Claims, No Drawings

PHARMACEUTICAL COMPOSITIONS COMPRISING HEMP AND TURMERIC TO TREAT PAIN AND INFLAMMATION

CROSS-REFERENCE TO RELATED APPLICATION

This PCT application claims priority and the benefit under 35 U.S.C. § 119(e) of U.S. Patent Application Ser. No. 61/989,158 filed May 6, 2014 entitled PHARMACEUTICAL COMPOSITIONS COMPRISING HEMP AND TURMERIC TO TREAT PAIN AND INFLAMMATION, the entire disclosure of which is incorporated by reference herein.

FIELD OF INVENTION

This invention relates to the use of hemp in combination with turmeric for the treatment of pain and inflammation. More specifically, CBD producing hemp and turmeric in various combinations and formulations can be used to treat pain at neurological level, cellular and molecular level.

BACKGROUND OF INVENTION

Pain is generally classified by type and includes, but is not limited to: acute pain and chronic pain caused by damage to tissue such as bone, muscle, or organs. The onset of pain is often accompanied by anxiety or emotional distress, tissue damage and nerve damage.

Cannabis extracts and synthetic cannabinoids are still widely considered illegal substances. Preclinical and clinical studies have suggested that the use of these substances may be useful to treat diverse diseases, including those related with acute or chronic pain. The discovery of cannabinoid receptors, their endogenous ligands, and the mechanism for the synthesis, transport, and degradation of these retrograde messengers, equips us with neurochemical tools for novel drug design. Agonist-activated cannabinoid receptors, modulate nociceptive thresholds, inhibit release of pro-inflammatory molecules, and display synergistic effects with other systems that influence analgesia, particularly the endogenous opioid system. Cannabinoid receptor agonists have shown therapeutic value against inflammatory and neuropathic pains, conditions that are often refractory to therapy. Although the psychoactive effects of these substances limited clinical progress on cannabinoid actions in pain mechanisms, preclinical research is progressing rapidly. For example, $CB_1$ mediated suppression of mast cell activation responses, $CB_2$-mediated indirect stimulation of opioid receptors located in primary afferent pathways, and the discovery of inhibitors for either the transporters or the enzymes degrading endocannabinoids are recent findings that suggest new therapeutic approaches to avoid central nervous system side effects. Examinations reveal promising indications of cannabinoid receptor agonists to alleviate acute and chronic pain episodes. Recently, *Cannabis sativa* extracts, containing known doses of tetrahydrocannabinol and cannabidiol (CBD), were granted approval in Canada for the relief of neuropathic pain in multiple sclerosis. Further double-blind placebo-controlled clinical trials are needed to evaluate the potential therapeutic effectiveness of various cannabinoid agonists-based medications for controlling different types of pain.

Curcumin, a phenolic compound present in *Curcuma longa*, has been reported to exert antinociceptive effects in some animal models. However, the mechanisms remain to be elucidated. This work aimed to investigate the antinociceptive action of curcumin on neuropathic pain and the underlying mechanism(s). Chronic constriction injury (CCI) in mice, a canonical animal model of neuropathic pain, was produced by loosely ligating the sciatic nerve in mice and von Frey hair or hot plate test was used to assess mechanical allodynia or thermal hyperalgesia (to heat), respectively. In this study, chronic, but not acute, curcumin treatment (5, 15 or 45 mg/kg, p.o., twice per day for three weeks) was shown to alleviated mechanical allodynia and thermal hyperalgesia in chronic construction injury (CCI) mice, accompanied by increasing spinal monoamine (or metabolite) contents. Chemical ablation of descending noradrenaline (NA) by 6-hydroxydopamine (6-OHDA), or depletion of descending serotonin by p-chlorophenylalanine (PCPA), abolished curcumin's antinociceptive effect on mechanical allodynia or thermal hyperalgesia, respectively. The anti-allodynic action of curcumin on mechanical stimuli was totally blocked by chronic co-treatment with the β(2)-adrenoceptor antagonist ICI 118,551, or by acute co-treatment with the delta-opioid receptor antagonist naltrindole. Meanwhile, co-treatment with the 5-HT(1A) receptor antagonist WAY-100635 chronically, or with the irreversible mu-opioid receptor antangonist β-funaltrexamine acutely, completely abrogated the anti-hyperalgesic action of curcumin on thermal stimuli. Collectively, these findings indicate that the descending monoamine system (coupled with spinal β(2)-adrenoceptor and 5-HT (1A) receptor) plays a role in the modality-specific antinociceptive effect of curcumin in neuropathic pain. Delta- and mu-opioid receptors are likely rendered as downstream targets, accordingly.

BRIEF SUMMARY OF THE INVENTION

The present invention comprises a composition for treating pain comprising a therapeutically effective amount of cannabidiol (CBD) and curcumin.

In certain embodiments, the composition further comprises at least one of: magnesium or ginger.

In certain embodiments, the CBD and curcumin of the composition comprises natural sources of CBD and curcumin. Preferably, the natural source of CBD comprises CBD producing hemp and the natural source of curcumin comprises turmeric. More preferably, CBD comprises a liquid or a powder extract of a cannabis plant and curcumin comprises a liquid or a powder extract from a turmeric root.

In certain embodiments of the composition, the CBD extract comprises at least 80% (w/w) CBD to total cannabinoid content. In certain embodiments of the composition, the curcumin extract comprises at least 2% by weight curcuminoid content.

In certain embodiments of the composition, the weight ratio of CBD extract to curcumin extract comprises about 1:1 to about 1:5. In certain embodiments of the composition, the weight ratio of CBD in the CBD extract and curcuminoid in the curcumin extract comprises about 1:1 to about 1:10.

In certain embodiments, the composition comprises a water soluble dosage form. The dosage form preferably comprises a capsule, tablet or liquid. More preferably, the dosage form comprises a tablet.

In certain embodiments, the composition comprises a tablet prepared under the conditions wherein the relative humidity (RH) is less than 30%.

The present invention also comprises a method of treating pain comprising the steps of: selecting a patient in need of treatment for pain and administering to the patient a therapeutically effective amount of CBD producing hemp and curcumin, wherein the patient is treated.

In certain embodiments, the pain comprises acute pain, chronic pain, or acute and chronic pain. In certain embodiments, patients are treated with a therapeutically effective amount of CBD and curcumin in the form of an inventive composition, such as those discussed above.

DETAILED DESCRIPTION OF THE INVENTION

The present invention comprises a method for the use of CBD producing hemp and turmeric in various combinations to treat pain at neurological level, cellular and molecular level. In a preferred embodiment, the present invention is a method of treating pain in patients which comprises administering to a patient in need thereof a therapeutically effective amount of at least one combination of hemp powder and curcumin powder.

Surprisingly, the combination of turmeric and cannabis treat pain much better than they treat individually. The combination allowed for better and longer duration of pain relief. According to the first aspect of the present invention there is provided a synergistic combination to treat pain.

The naturally occurring cannabinoid are safer than synthetic. Both plant materials, hemp and turmeric, are safe and very effective to treat pain. Both have the mode of action to treat pain that is different and the combination has a potentiating and synergistic effects.

According to an aspect of the invention, the combination of cannabidiol (CBD) and curcumin containing components are administered in a composition to treat pain. The CBD and curcumin are preferably derived from natural sources. More preferably, the CBD comprises CBD producing hemp. More preferably, the curcumin comprises turmeric.

In an embodiment, the CBD component comprises either a liquid or powder extract of a CBD containing plant, preferably a cannabis plant. Preferably, CBD in the extract comprises at least 80% by weight of CBD to total cannabinoid content. More preferably, the CBD is at least 90%. Even more preferably, the CBD is at least 95%. Most preferably, the CBD is at least 99%.

In an embodiment, the curcumin component comprises either a liquid or powder extract of a curcumin containing plant, preferably a turmeric root. Preferably, the curcumin extract comprises at least 2% by weight of curcuminoid content. More preferably, the curcumin extract comprises at least 3% by weight of curcuminoid content. Even more preferably, the curcumin extract comprises at least 5% by weight of curcuminoid content. Most preferably, the curcumin extract comprises about 6-12.5% by weight of curcuminoid content.

CBD may refer to the cannabidiol compound or more generally to a CBD containing component. Cannabis may refer to CBD with the scope of CBD as detailed above. Likewise, curcumin may refer to the curcumin compound, curcuminoids or more generally to a curcumin containing component, for example and as often seen, interchangeably or in conjunction with turmeric in nutraceuticals.

In an embodiment, the curcumin to CBD ratio in the combination composition may range from 1:1 to 1:5 and more preferably specifically: 1:1; 1:1.5; 1:2 or 1:5. In another embodiment, the curcumin to CBD ratio, and more specifically the CBD to curcuminoid ratio, may range from 1:1 to 1:10. Preferably, the ratios may be any of 1:1, 1:2, 1:3, 1:5 and 1:10.

According to an aspect of the invention, the composition may further comprise one or more components that contribute to or potentiate the pain relieving effects of CBD or curcumin. For example, the composition may comprise magnesium. The composition may also further comprise ginger. In an embodiment, ginger is an extract comprising polyphenols from *z. officinale*.

According to an aspect of the invention, the combination of CBD and curcumin containing components are administered in a composition to treat pain comprising a water soluble dosage form.

In an embodiment, the invention combination maybe, for example, administered locally. The components of the invention maybe, for example, administered topically. The components of the invention maybe, for example, mixed with pharmaceutically suitable auxiliaries, e.g., as described in the standard reference, Gennaro et al., Remington's Pharmaceutical Sciences. By means of pharmaceutically suitable liquids the components may be applied in the form of, for example, a solution, suspension, or emulsion. The components may also be formulated in, for example, a patch, ointment or can be enclosed in a device for local administration to the skin.

In an embodiment, the invention combination maybe, for example, enterally and mixed with pharmaceutically suitable auxiliaries, e.g., as described in the standard reference, Gennaro et al., Remington's Pharmaceutical Sciences, 2005. The components may be compressed into solid dosage units, such as pills, tablets, or be processed into capsules or suppositories. By means of pharmaceutically suitable liquids the components can also be in the form of a solution, suspension, emulsion.

For making dosage units, e.g., tablets, the use of conventional additives such as fillers, colorants, polymeric binders and the like is contemplated. In general, any pharmaceutically acceptable additive which does not interfere with the function of the active components can be used. Suitable carriers with which the compositions can be administered include lactose, starch, cellulose derivatives and the like, or mixtures thereof, used in suitable amounts.

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E 100, may be particularly suitable for taste masking applications. Traditional enteric coating materials listed elsewhere can also be applied to form an isolating layer.

The above dosage forms will also include the necessary carrier material, excipient, lubricant, buffer, antibacterial, bulking agent (such as mannitol), anti-oxidants (ascorbic acid of sodium bisulfite) or the like.

Liquid formulations can also be prepared by dissolving or suspending one or the combination of the components in a conventional liquid vehicle acceptable for administration.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

According to an aspect of the invention, the composition comprises a tablet prepared under conditions where the relative humidity (RH) is kept under 30%.

EXAMPLES

The following are examples of the present invention in a preferred embodiment. Although the invention is explained in relation to its preferred embodiments, it is to be understood that many other possible modifications and variations can be made without departing from the spirit and scope of the invention.

Example I

The following Table 1 lists a tablet formulation of a preferred embodiment of the present invention.

TABLE 1

| Ingredients | Amount (mg) Example 1 |
|---|---|
| Cannabis: Curcumin | 75.00 |
| Microcrystalline Cellulose | 24.20 |
| Corn starch | 00.00 |
| Starch Pregelatinized | 7.70 |
| Silica Colloidal Anhydrous | 2.20 |
| Stearic Acid | 0.90 |
| Talc | 3.33 |

TABLE 1-continued

| Ingredients | Amount (mg) Example 1 |
|---|---|
| Methacrylic Acid-Ethyl Acrylate Copolymer (1:1) | 10.50 (as dry substance) |
| Triethyl Citrate | 1.05 |
| Simethicone Emulsion | 0.12 (as dry substance) |
| Purified Water | q.s |

Example II

The following is a preferred embodiment for preparing the tablet formulation in Example I.

1. Grinding of curcumin and Cannabis to fine powder, sifting the powder, microcrystalline cellulose, corn starch and polymer,
2. Blending the material of step 1,
3. Sifting the pregelatinized starch and silica colloidal anhydrous and adding it to the material of step 2,
4. Sifting the stearic acid and adding to material of step 3 and blending,
5. Compacting the material of step 4 in a horizontal feed roller compactor,
6. Milling the compacts in oscillating granulator to achieve desired sized granules,
7. Compressing the granules of step 6,
8. Preparing the enteric coating dispersion by adding and mixing talc, methacrylic acid-ethyl acrylate copolymer (1:1), triethylcitrate and simethicone emulsion in water,
9. Spraying the dispersion onto the tablet.

Example III

The following is a preferred embodiment for preparing the tablet formulation in Example I, under conditions where the relative humidity (RH) is maintained below 30%.

1. Cannabis+curcumin, microcrystalline cellulose/corn starch were sifted through appropriate sieve;
2. The above ingredients were mixed in a blender;
3. Pregelatinized starch silica colloidal anhydrous were sifted through appropriate sieve and added to material of step 2 and mixed in a blender;
4. Stearic acid was sifted through appropriate sieve;
5. Material of step 4 was added to the material of step 3 and mixed in a blender;
6. The above blend was compressed using approved punches and dies;
7. Enteric coating dispersion was prepared by adding and mixing talc, methacrlic acid-ethyl acrylate copolymer (1:1), triethyl citrate, and simethicone emulsion in water; and
8. The dispersion was sprayed onto the tablets in a coating pan.

Example IV

The following Table 2 lists a tablet formulation of a preferred embodiment of the present invention that may be prepared in the same processes detailed in Examples II and III above.

TABLE 2

| Ingredients | Amount (mg) Example II |
|---|---|
| Cannabis: Curcumin | 75.00 |
| Microcrystalline Cellulose | 00.00 |
| Corn starch | 24.20 |
| Starch Pregelatinized | 7.70 |
| Silica Colloidal Anhydrous | 2.20 |
| Stearic Acid | 0.90 |
| Talc | 3.33 |
| Methacrylic Acid-Ethyl Acrylate Copolymer (1:1) | 10.50 (as dry substance) |
| Triethyl Citrate | 1.05 |
| Simethicone Emulsion | 0.12 (as dry substance) |
| Purified Water | q.s |

Example V

A capsule formulation of the present invention can be prepared for 120,000 capsules of 500 mg each with the following components: 120 kg of cannabis powder, 240 kg of curcumin powder, 7 kg of polymer, 10 kg of magnesium sulfate.

Example VI

A liquid formulation of the present invention can be prepared with: 10 liter of CBD extract and 10 liter of curcumoid extract and 50 liter of syrup with stabilizers.

Example VII

The following Table 4 shows the pain relief achieved in a 7 volunteer study. Patients taking singly, curcumin or CBD showed partial pain relief for no more than 8 hours. The same patients taking the combination of curcumin and CBD showed comparable pain relief for 24 hours. In one case, a patient achieved total pain relief.

TABLE 4

| Subject and pain type | Relief with Curcumin (30 mg) | Relief with Hemp CBD (20 mg) | Relief with Hemp CBD (20 mg) + Curcumin (30 mg) |
|---|---|---|---|
| 1. Male(California) Joint pain | Partial relief | Partial relief | 24 hours relief |
| 2. Female (California) Migraine | Partial relief | Partial relief | 24 hours relief |
| 3. Male (India) Crohn's | Partial relief | Partial relief | 24 hours relief |
| 4. Male (Colorado) Back pain | Partial relief | Partial relief | 24 hours relief |
| 5. Male(California) Back pain | Partial relief | Partial relief | 24 hours relief |
| 6. Female(California) Body aches | NA | NA | Total relief in 30 minutes |
| 7. Male(Colorado) Joint pain | NA | NA | 24 ours relief |

All of the above formulations contain magnesium. Patients received the combination of CBD and curcumin in the following formulation comprising: (a) hemp derived terpiniods and oil; (b) turmeric as curcumin and; (c) magnesium.

REFERENCES

1. U.S. Pat. No. 6,630,507
2. Zahao, X. et. al., "Curcumin exerts antinociceptive effects in a mouse model of neuropathic pain: descending monoamine system and opioid receptors are differentially involved," *Neuropharmacology*, February 2012 62(2): 843-54.

What is claimed is:

1. A tablet or capsule consisting essentially of curcumin, cannabidiol, talc, methacrylic acid-ethyl acrylate copolymer, triethyl citrate, and a simethicone emulsion.
2. The composition of claim 1, further consisting essentially of a component selected from the group consisting of magnesium and ginger.
3. The composition of claim 1, wherein the cannabidiol and curcumin are from natural sources.
4. The composition of claim 1, wherein the natural source of cannabidiol is hemp and the natural source of curcumin is turmeric.
5. The composition of claim 4, wherein the cannabidiol is a liquid or a powder extract of cannabis and the curcumin is a liquid or a powder extract from a turmeric root.
6. The composition of claim 5, wherein the cannabidiol extract is at least 80% (w/w) cannabidiol to the total cannabinoid content in the composition.
7. The composition of claim 5, wherein the curcumin extract is at least 2% by weight curcuminoid.
8. The composition of claim 5, wherein the weight ratio of cannabidiol extract to curcumin extract is about 1:1 to about 1:5.
9. The composition of claim 5, wherein the weight ratio of cannabidiol in the cannabidiol extract and curcuminoid in the curcumin extract is about 1:1 to about 1:10.
10. The composition of claim 5, wherein the composition is a water soluble dosage form.
11. The dosage form of claim 10, wherein the dosage form is a capsule, tablet or liquid.
12. The dosage form of claim 11, wherein the dosage form is a capsule.
13. A method of treating pain in a human consisting essentially of:
    a) selecting a human in need of treatment for pain;
    b) administering to the patient in need of treatment for pain a therapeutically effective amount of tablet or capsule consisting essentially of curcumin, cannabidiol, talc, methacrylic acid-ethyl acrylate copolymer, triethyl citrate, and a simethicone emulsion, wherein the patient in need of treatment for pain is effectively treated.
14. The method as claimed in claim 13, wherein the pain is selected from the group consisting of acute pain and chronic pain.
15. A method of treating pain consisting essentially of administering to a patient in need of treatment for pain the composition of claim 2.
16. A method of treating pain consisting essentially of administering to a patient in need of treatment for pain the composition of claim 4.
17. A method of treating pain consisting essentially of administering to a patient in need of treatment for pain the composition of claim 5.
18. A method of treating pain consisting essentially of administering to a patient in need of treatment for pain the capsule of claim 12.

* * * * *